(12) United States Patent
Whitfield et al.

(10) Patent No.: US 11,376,000 B2
(45) Date of Patent: Jul. 5, 2022

(54) SURGICAL STAPLER ANVIL WITH DIRECTIONALLY BIASED STAPLE POCKETS

(71) Applicant: Covidien LP, Mansfield, MA (US)

(72) Inventors: Kenneth H. Whitfield, North Haven, CT (US); Roanit A. Fernandes, Hyderabad (IN); Anthony Gaddy, Windsor, CT (US)

(73) Assignee: COVIDIEN LP, Mansfield, MA (US)

( * ) Notice: Subject to any disclaimer, the term of this patent is extended or adjusted under 35 U.S.C. 154(b) by 144 days.

(21) Appl. No.: 16/788,669

(22) Filed: Feb. 12, 2020

(65) Prior Publication Data

US 2020/0289112 A1 Sep. 17, 2020

Related U.S. Application Data

(60) Provisional application No. 62/817,854, filed on Mar. 13, 2019.

(51) Int. Cl.
*A61B 17/072* (2006.01)

(52) U.S. Cl.
CPC .. *A61B 17/072* (2013.01); *A61B 2017/07264* (2013.01); *A61B 2017/07271* (2013.01)

(58) Field of Classification Search
CPC  A61B 2017/07235; A61B 2017/07242; A61B 2017/0725; A61B 2017/07257; A61B 2017/07264
USPC ...................................................... 227/175.1
See application file for complete search history.

(56) References Cited

U.S. PATENT DOCUMENTS

| 5,350,400 | A  | * | 9/1994  | Esposito | A61B 17/0686 606/219 |
| 6,905,057 | B2 | * | 6/2005  | Swayze   | A61B 17/07207 227/176.1 |
| 8,308,040 | B2 | * | 11/2012 | Huang    | A61B 17/07207 227/175.1 |

(Continued)

FOREIGN PATENT DOCUMENTS

| EP | 2452634 A2 | 5/2012 |
| EP | 2772195 A2 | 9/2014 |

(Continued)

OTHER PUBLICATIONS

European Search Report dated Jun. 19, 2020, issued in EP Appln. No. 20162612, 9 pages.

*Primary Examiner* — Valentin Neacsu
(74) *Attorney, Agent, or Firm* — Carter, DeLuca & Farrell LLP

(57) ABSTRACT

An end effector for a surgical stapling apparatus includes a cartridge assembly and an anvil assembly. The cartridge assembly supports staples. Each staple includes a backspan, a first leg, and a second leg. The first and second legs extend from the backspan. The anvil assembly is coupled to the cartridge assembly. The anvil assembly includes an anvil having opposed side surfaces. The anvil defines a knife slot and biased staple-forming pockets disposed between the opposed side surfaces of the anvil. Each biased staple-forming pocket is positioned to form the first and second legs of a respective staple on one side of the backspan of the respective staple. The one side of the backspan is positioned toward the knife slot of the anvil relative to the opposed side surfaces of the anvil.

15 Claims, 5 Drawing Sheets

(56) References Cited

U.S. PATENT DOCUMENTS

| | | | | |
|---|---|---|---|---|
| 8,424,735 | B2* | 4/2013 | Viola | A61B 17/07207 |
| | | | | 227/175.1 |
| 8,448,832 | B2* | 5/2013 | Viola | A61B 17/0644 |
| | | | | 227/175.1 |
| 8,684,249 | B2* | 4/2014 | Racenet | A61B 17/072 |
| | | | | 227/176.1 |
| 8,905,287 | B2* | 12/2014 | Racenet | A61B 17/068 |
| | | | | 227/176.1 |
| 9,463,017 | B2* | 10/2016 | Viola | A61B 17/105 |
| 9,517,066 | B2* | 12/2016 | Racenet | A61B 17/068 |
| 9,687,232 | B2* | 6/2017 | Shelton, IV | A61B 34/37 |
| 2004/0006372 | A1* | 1/2004 | Racenet | A61B 17/072 |
| | | | | 606/219 |
| 2005/0267530 | A1* | 12/2005 | Cummins | A61B 17/0644 |
| | | | | 606/219 |
| 2005/0283190 | A1* | 12/2005 | Huitema | A61B 17/0644 |
| | | | | 606/219 |
| 2009/0255978 | A1* | 10/2009 | Viola | A61B 17/105 |
| | | | | 227/180.1 |
| 2011/0087276 | A1* | 4/2011 | Bedi | A61B 17/07207 |
| | | | | 606/219 |
| 2012/0080487 | A1* | 4/2012 | Woodard, Jr. | A61B 17/08 |
| | | | | 227/176.1 |
| 2013/0172928 | A1* | 7/2013 | Kostrzewski | A61B 17/07207 |
| | | | | 606/219 |
| 2013/0172929 | A1* | 7/2013 | Hess | A61B 17/1155 |
| | | | | 606/219 |
| 2014/0110457 | A1* | 4/2014 | Zhang | A61B 17/068 |
| | | | | 227/177.1 |
| 2017/0055996 | A1* | 3/2017 | Baxter, III | A61B 17/07292 |
| 2017/0055997 | A1* | 3/2017 | Swayze | A61B 17/07207 |
| 2018/0168597 | A1* | 6/2018 | Fanelli | A61B 34/30 |
| 2018/0168620 | A1* | 6/2018 | Huang | A61B 34/30 |
| 2018/0235619 | A1* | 8/2018 | Harris | A61B 17/07207 |

FOREIGN PATENT DOCUMENTS

| | | |
|---|---|---|
| EP | 3338714 A2 | 6/2018 |
| EP | 3363378 A1 | 8/2018 |
| KR | 20150075510 A | 7/2015 |

* cited by examiner

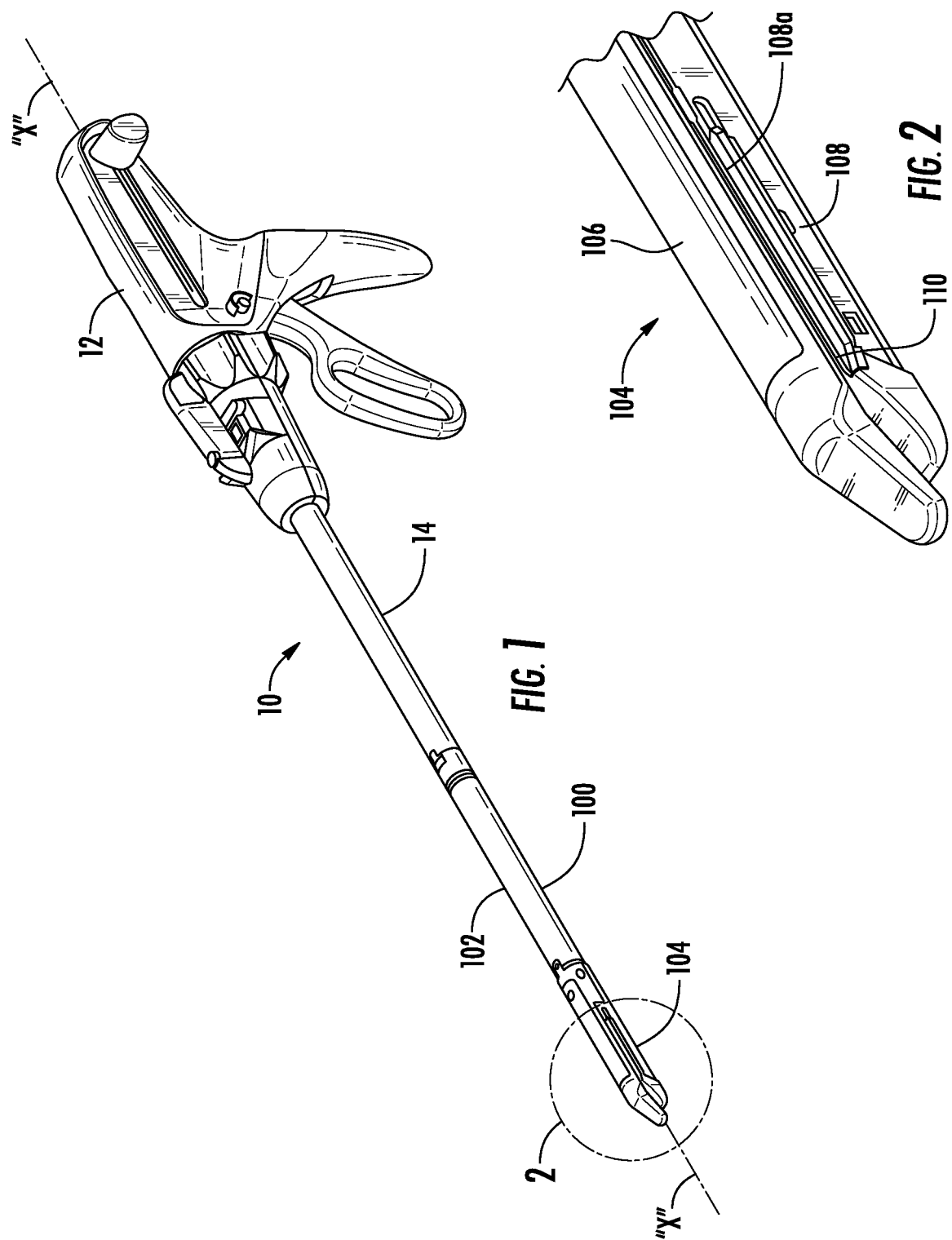

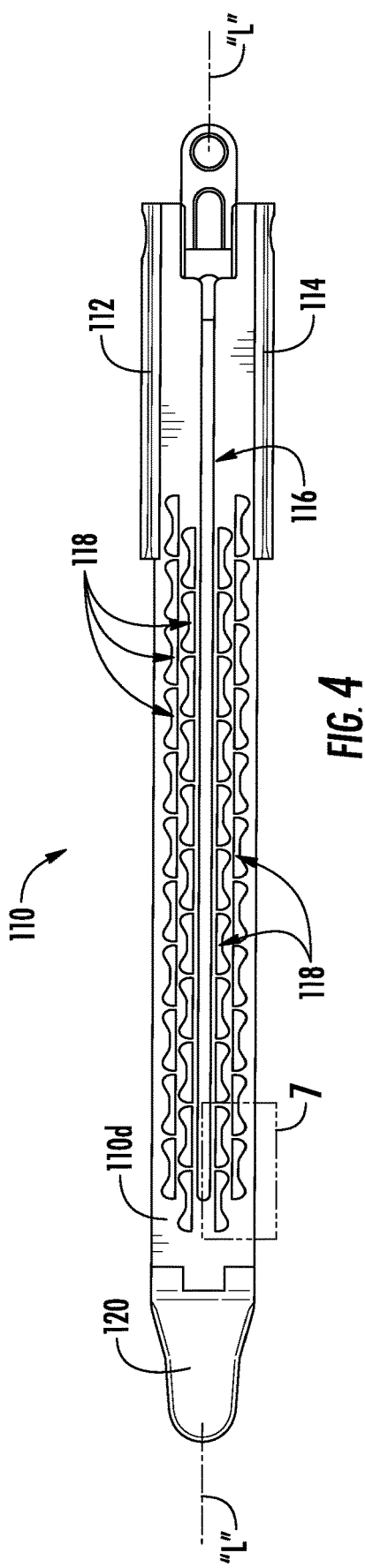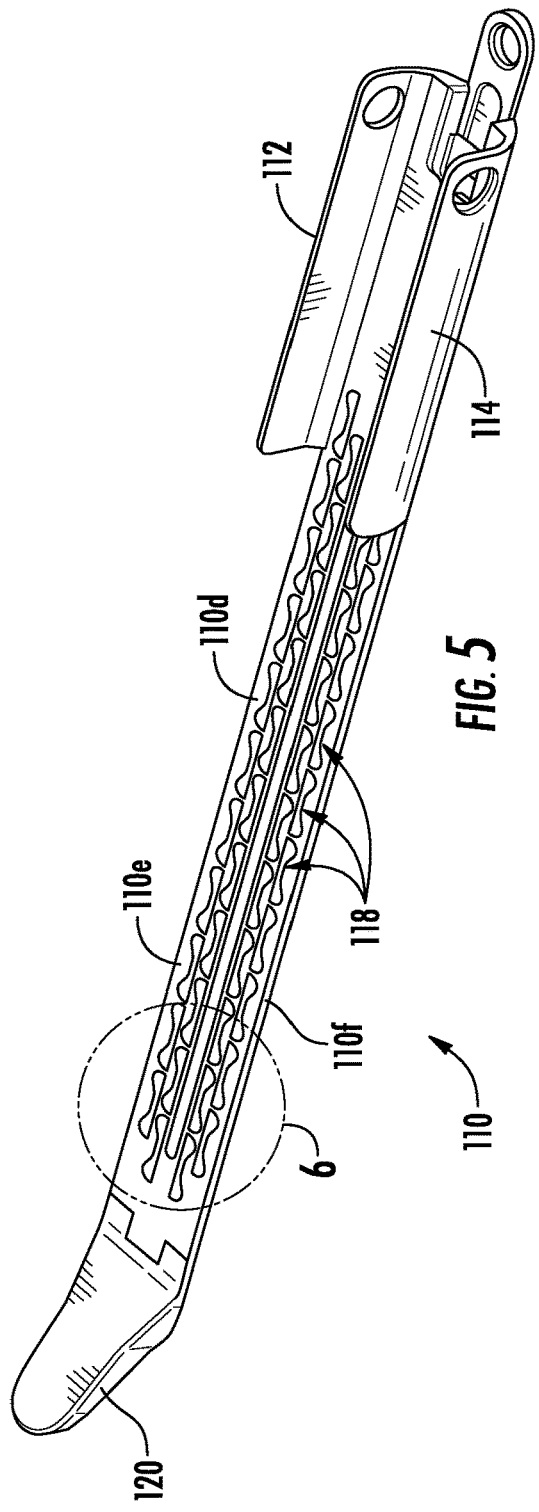

SURGICAL STAPLER ANVIL WITH DIRECTIONALLY BIASED STAPLE POCKETS

CROSS-REFERENCE TO RELATED APPLICATIONS

This application claims the benefit of U.S. Patent Application Ser. No. 62/817,854, filed on Mar. 13, 2019, the entire contents of which are incorporated by reference herein.

TECHNICAL FIELD

This disclosure relates to surgical stapling apparatus, devices and/or systems for performing surgical procedures and methods of use thereof.

BACKGROUND

Surgical stapling apparatus that clamp, cut and/or staple tissue are well known in the art. Such surgical stapling apparatus include end effectors having two elongated jaw members used to capture or clamp tissue. One of the two jaw members usually carries a staple cartridge that houses a plurality of staples positioned in rows, while the other of the two jaw members has an anvil for forming the staples as the staples are driven from the staple cartridge. For instance, in linear surgical stapling apparatus, a stapling operation is effectuated by a cam bar, a drive sled or other similar mechanism having a cam member that travels longitudinally through channels defined in the staple cartridge and acts upon staple pushers in the channels to sequentially eject linear rows of staples from the staple cartridge. A knife is movably positioned between the linear rows of staples such that when the surgical stapling apparatus is positioned about tissue and actuated, the tissue is joined and/or simultaneously or nearly simultaneously cut.

SUMMARY

According to one aspect of the disclosure, an end effector for a surgical stapling apparatus includes a cartridge assembly and an anvil assembly. The cartridge assembly supports a plurality of staples. Each staple of the plurality of staples includes a backspan, a first leg, and a second leg. The first and second legs extend from the backspan. The anvil assembly is coupled to the cartridge assembly. The anvil assembly includes an anvil having opposed side surfaces. The anvil defines a knife slot and a plurality of biased staple-forming pockets disposed between the opposed side surfaces of the anvil. Each biased staple-forming pocket of the plurality of biased staple-forming pockets is positioned to form the first and second legs of a respective staple of the plurality of staples on one side of the backspan of the respective staple. The one side of the backspan is positioned toward the knife slot of the anvil relative to the opposed side surfaces of the anvil.

In some embodiments, the plurality of biased staple-forming pockets may be arranged in one or more linear rows. The linear rows may include an inner row and an outer row. The inner and outer rows may be longitudinally offset from one another.

In embodiments, the end effector may include a dissecting tip that extends distally from the anvil.

In various embodiments, each biased staple-forming pocket of the plurality of biased staple-forming pockets may include a first staple-leg forming cavity and a second staple-leg forming cavity. Each of the first and second staple-leg forming cavities may include a guide portion and a spine portion. The guide portion may be configured to funnel one of the first or second legs of one of the staples of the plurality of staples toward the spine portion. The first and second staple-leg forming cavities may be separated by a central bridge portion. The central bridge portion may ascend from a bottom surface of the first and second staple-leg forming cavities. Each biased staple-forming pocket may include an end wall that extends linearly along the first and second staple-leg forming cavities and the central bridge portion on a medial side toward the knife slot. The anvil may define a longitudinal axis that extends along a length of the anvil. The end wall may be parallel to the longitudinal axis of the anvil.

According to another aspect of the disclosure, a surgical stapling apparatus includes a housing assembly and a shaft assembly operatively coupled to the housing assembly and supporting an end effector. The end effector includes a staple cartridge and an anvil. The staple cartridge supports a plurality of staples. Each staple of the plurality of staples includes a backspan, a first leg, and a second leg. The first and second legs extend from the backspan. The anvil has opposed side surfaces and defines a knife slot and a plurality of biased staple-forming pockets positioned adjacent to the knife slot. The knife slot and the plurality of biased staple-forming pockets are disposed between the opposed side surfaces of the anvil. Each biased staple-forming pocket of the plurality of biased staple-forming pockets is configured to form the first and second legs of a respective staple of the plurality of staples on one side of the backspan of the respective staple. The one side of the backspan is positioned toward the knife slot of the anvil relative to the opposed side surfaces of the anvil.

In some embodiments, the plurality of biased staple-forming pockets is arranged in linear rows on opposite sides of the knife slot. The linear rows may include an inner row and an outer row on each of the opposite sides of the knife slot.

In certain embodiments, the surgical stapling apparatus may further include a dissecting tip that extends distally from the anvil.

In various embodiments, each biased staple-forming pocket of the plurality of biased staple-forming pockets may include a first staple-leg forming cavity and a second staple-leg forming cavity. The first and second staple-leg forming cavities may be separated by a central bridge portion. Each biased staple-forming pocket may include an end wall disposed in parallel relation to the knife slot.

According to still another aspect of the disclosure, a method of forming staples includes firing staples supported in a staple cartridge into an anvil operatively coupled to the staple cartridge. The method further involves forming the staples in biased staple-forming pockets defined in the anvil such that both legs of each formed staple are positioned on one side of a backspan of the respective staple, the one side of the backspan being positioned toward a longitudinal axis of the anvil.

In aspects, forming the staples may include forming the staples in linear rows on both sides of a knife slot defined in the anvil.

In some aspects, forming the staples may include forming the staples in longitudinally offset linear rows.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 1 is a perspective view of a surgical stapling apparatus in accordance with the principles of the disclosure;

FIG. 2 is an enlarged, perspective view of the indicated area of detail shown in FIG. 1;

FIG. 4 is a bottom view of the anvil of FIG. 3;

FIG. 5 is a perspective view of the anvil of FIGS. 3 and 4;

DETAILED DESCRIPTION

Figure 3:
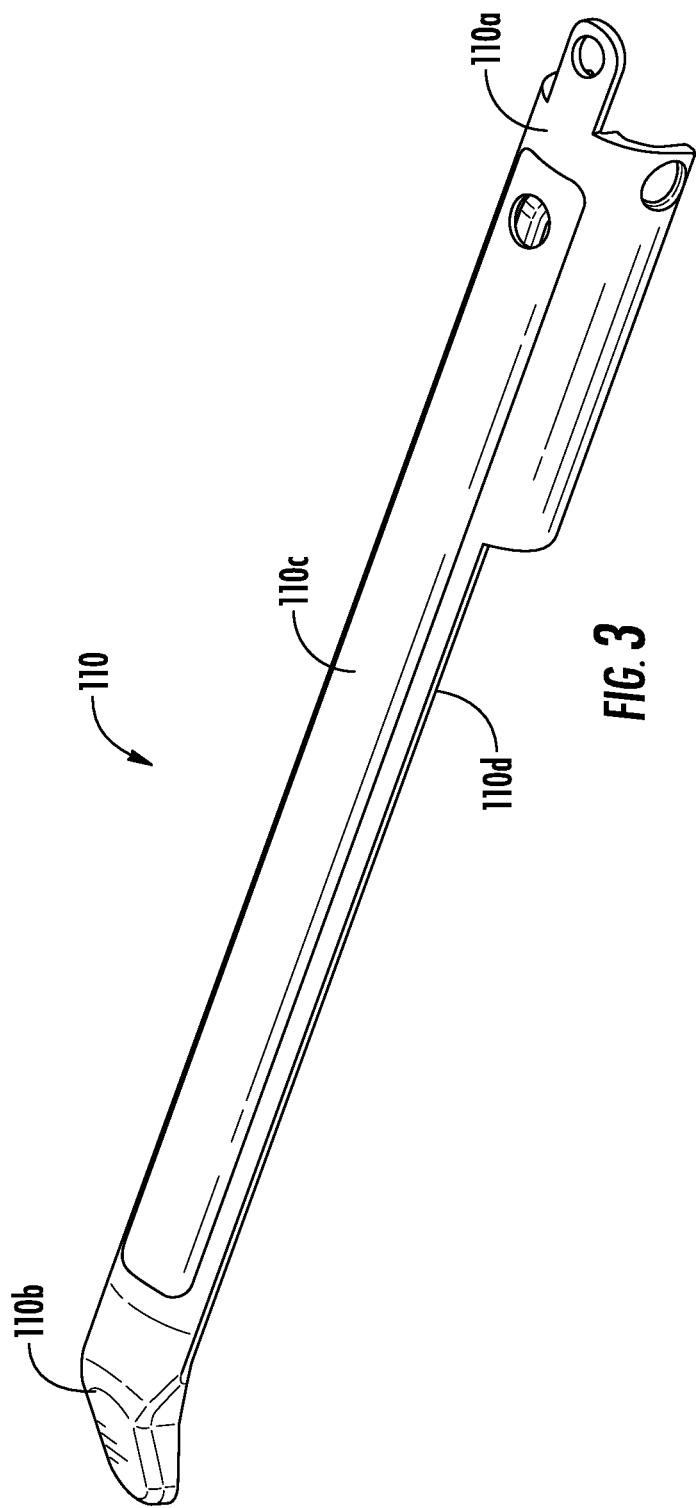
FIG. 3 is a top, perspective view of an anvil of the surgical stapling apparatus of FIG. 1.

Embodiments of the presently disclosed surgical stapling apparatus are described in detail with reference to the drawings, in which like reference numerals designate identical or corresponding elements in each of the several views. As commonly known, the term "clinician" refers to a doctor, a nurse, or any other care provider and may include support personnel. Additionally, the term "proximal" refers to the portion of structure that is closer to the clinician and the term "distal" refers to the portion of structure that is farther from the clinician. In addition, directional terms such as front, rear, upper, lower, top, bottom, and the like are used simply for convenience of description and are not intended to limit the disclosure attached hereto.

As used herein, the terms parallel and perpendicular are understood to include relative configurations that are substantially parallel and substantially perpendicular up to about + or −10 degrees from true parallel and true perpendicular.

In the following description, well-known functions or constructions are not described in detail to avoid obscuring the present disclosure in unnecessary detail.

This disclosure describes surgical stapling apparatus that achieves superior hemostasis on tissues by having staple tips and legs of surgical staples formed to a single side of a backspan of the staples and positioned medially towards a knife cut. Having a plurality of staples formed on tissue in this manner effectively and hemostatically seals off the blood flow by having the staple tips positioned on a medial side of the staple relative to the anvil (e.g., toward the knife cut and away from a blood pressure side) to prevent staple tip punctures that create leak paths.

Formed surgical staples, as deposited on human vessels, tubular structures, and organ tissues by surgical stapling apparatus can influence the reduction of bleeding, oozing of blood, and air leaks by having the staples formed medially, particularly when the entire plurality of staples is formed such that the piercing tips and legs of the staples are positioned to a medial side of the staple backspan relative to the anvil to affect a vast improvement in hemostasis. To form the staples in this manner, the staple pockets of the anvil of the surgical stapling apparatus of this disclosure have a staple-forming shape designed to influence both staple legs toward the knife cut and away from a blood pressure side (e.g., in a medial direction during formation). Having anvil staple pockets that form staples on tissue in this manner provides staple formation with superior hemostasis. In particular, the disclosed anvil and/or staple pockets are configured to form the staple legs (typically in the form of a "B" or other shaped profile) to one side of the staple backspan, and more specifically, towards the medial direction closest to the staple line knife cut.

With reference to FIGS. 1 and 2, a surgical stapling apparatus 10 of this disclosure includes a housing assembly 12 (which may include one or more handles that may be manually actuatable to fire surgical stapling apparatus 10), an adapter assembly 14 secured to housing assembly 12 and extending distally from housing assembly 12, and a loading unit 100 secured to adapter assembly 14 and extending distally from adapter assembly 14. Adapter assembly 14 and loading unit 100 define a longitudinal axis "X-X" that extends longitudinally therealong. Loading unit 100 may be disposable and/or include one or more disposable components.

Loading unit 100 of surgical stapling apparatus 10 is releasably secured to a distal end portion of adapter assembly 14 and includes a shaft assembly 102 that supports an end effector 104 on a distal end portion of shaft assembly 102. End effector 104 includes an anvil assembly 106 and a cartridge assembly 108 that houses a plurality of staples (not shown) in a reload or cartridge 108a thereof that may be selectively replaceable. Anvil assembly 106 includes an anvil 110 against which the plurality of staples is formed upon a firing of surgical stapling apparatus 10.

For a more detailed description of similar stapling apparatus, or components thereof, reference can be made, for example, to U.S. Pat. No. 9,713,470 to Scirica et al. and U.S. Pat. No. 8,070,033 to Milliman et al., the entire contents of each of which are incorporated herein by reference.

Turning now to FIGS. 3-5, anvil 110 of anvil assembly 106 defines a longitudinal axis "L-L" that extends from a proximal end portion 110a to a distal end portion 110b of anvil 110. Anvil 110 also includes a top surface 110c, which may be arcuate or radial, and a bottom surface 110d, which may be planar. Anvil 110 further includes side surfaces 110e, 110f. Anvil 110 includes tissue stops 112, 114 that extend downwardly from proximal end portion 110a of anvil 110 to limit proximal movement of tissue disposed between anvil and cartridge assemblies 106, 108 of surgical stapling apparatus 10. Tissue stops 112, 114 may have planar inner surfaces and/or radial outer surfaces. Anvil 110 defines a knife slot 116 that is recessed into bottom surface 110d of anvil 110 and extends along longitudinal axis "L-L" of anvil 110 (e.g., centered on longitudinal axis "L-L." Knife slot 116 extends longitudinally along anvil 110, and less than a full length of anvil 110, to receive and facilitate axial translation of a knife (not shown) or an I-beam (not shown) supporting a knife of surgical stapling apparatus 10 therethrough for cutting tissue disposed between anvil and cartridge assemblies 106, 108 of surgical stapling apparatus 10.

As seen in FIG. 4, there is an inner linear row of biased staple-forming pockets 118 and an outer linear row of biased staple-forming pockets 118 defined in bottom surface 110d of anvil 110 on both sides of knife slot 116 of anvil 110 so that there are four linear rows of biased staple-forming pockets 118 on anvil 110. Other embodiments may include any number of rows of biased staple-forming pockets 118 on either side of knife slot 116 (e.g., three or four rows on either and/or both sides). Biased staple-forming pockets 118 may be formed using any suitable manufacturing technique such as coining with a metal coining die or electrical discharge machining (EDM). For instance, the EDM process may involve spark machining, spark eroding, burning, die sinking, wire burning, wire erosion, use of metal electrodes, etc., or combinations thereof. The rows of biased staple-forming pockets 118 are arranged in parallel relation to one another and knife slot 116 (e.g., parallel to longitudinal axis "L-L" and length of anvil 110). The rows of biased staple-forming pockets 118 are disposed on opposite sides of knife slot 116 and positioned to form staples 200 (see FIGS. 9A and 9B) supported in cartridge 108a of cartridge assembly 108 in a medial direction toward knife slot 116.

As can be appreciated, each biased staple-forming pocket 118 in a row may be longitudinally offset a substantially equal distance from the next or adjacent biased staple-forming pocket 118 to constitute a pitch, an array, or a pattern.

As seen, for example, in FIGS. 4 and 5, distal end portion 110b of anvil 110 includes a dissecting tip 120 to facilitate dissection of tissue, but in some embodiments, distal end portion 110b of anvil 110 may have a blunt or rounded tip (not shown). Dissecting tip 120 maybe angled relative to the longitudinal axis between about 5 degrees to about 90 degrees. Dissecting tip 120 tapers distally such that dissecting tip 120 has a proximal portion width that is greater than a distal portion width. A distal portion of dissecting tip 120 may have a rounded or radial configuration. In some embodiments dissecting tip 120 is integrally formed with anvil 110, and in some embodiments, dissecting tip 120 is detachably connected to anvil 110. In some embodiments, dissecting tip 120 may be made at least partially from metal such as stainless steel. In certain embodiments, dissecting tip 120 may be made at least partially from a nonmetallic material such as a rigid polymeric material.

Figure 6:
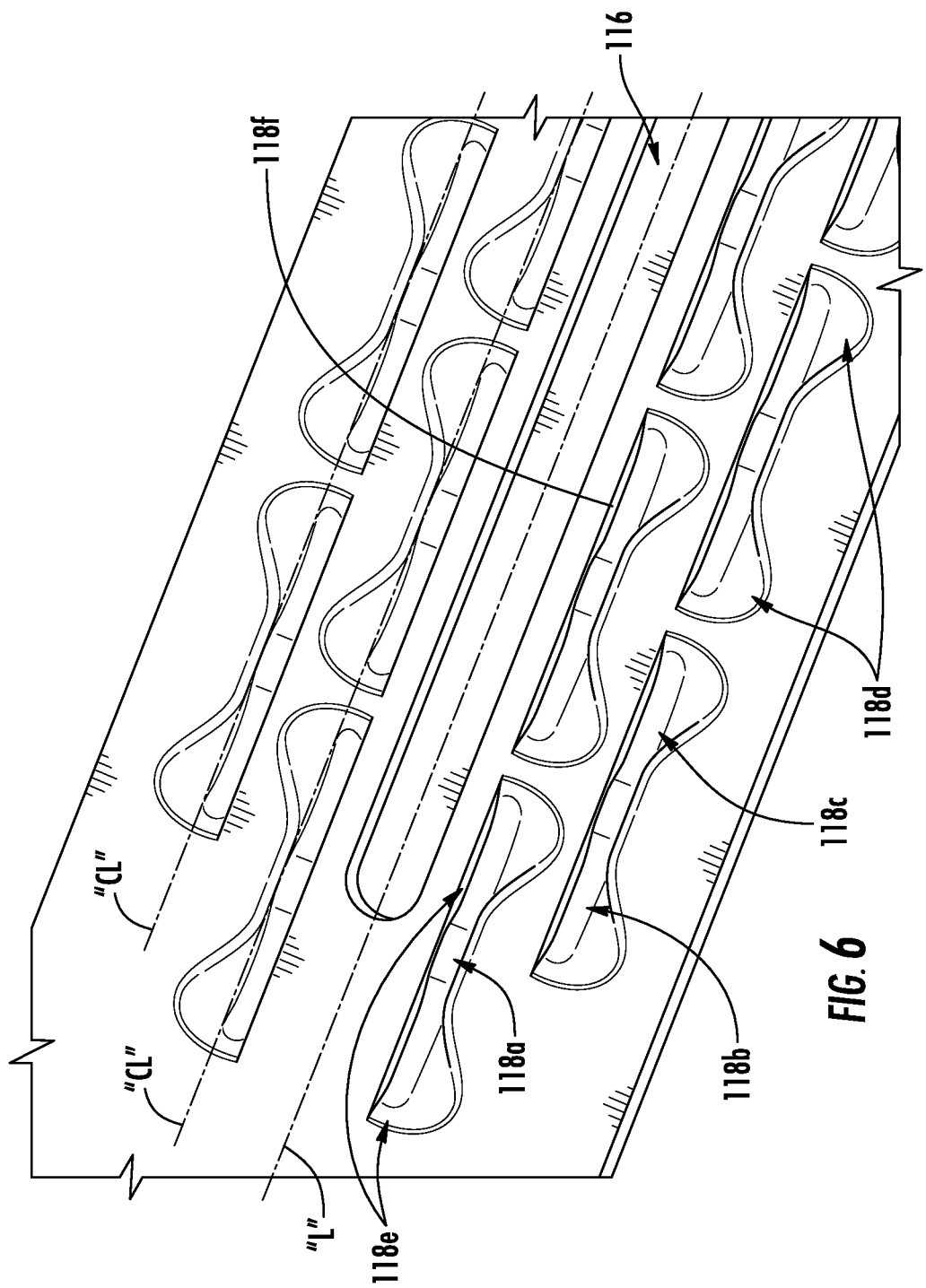
FIG. 6 is an enlarged view of the indicated area of detail shown in FIG. 5.
Figure 7:
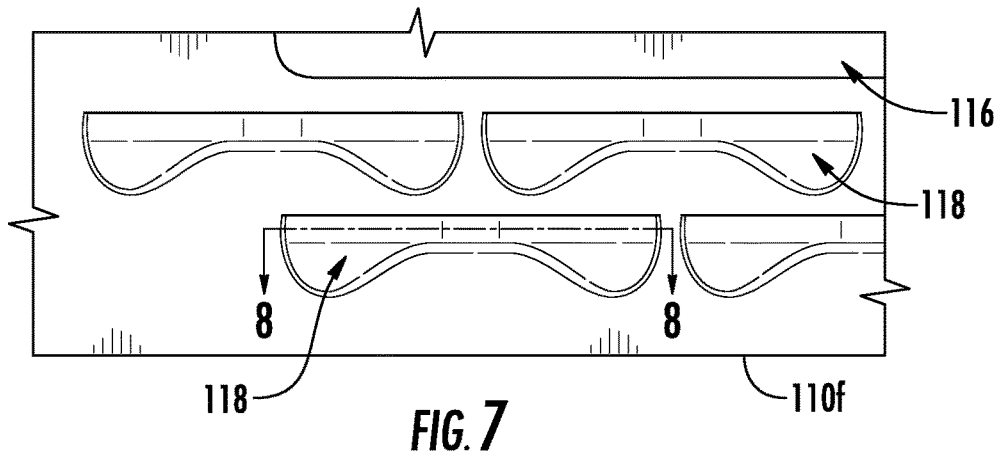
FIG. 7 is an enlarged view of the indicated area of detail shown in FIG. 4.
Figure 8:
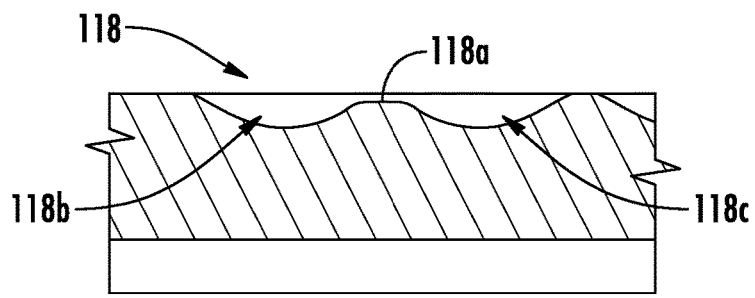
FIG. 8 is a cross-sectional view of a staple pocket of the anvil of FIGS. 3-5 as taken along section line 8-8.

With reference to FIGS. 6-8, biased staple-forming pockets 118 of anvil 110 include a central bridge portion 118a that separates a first staple-leg forming cavity 118b, and a second staple leg forming cavity 118c. First and second staple-leg forming cavities 118b, 118c may have a substantially equal depth. Each of first and second staple-leg forming cavities 118b, 118c has a concave, arcuate configuration and includes a guide portion 118d that receives a staple leg 200a of a staple 200 and funnels staple leg 200a in a medial direction into a spine portion 118e to guide formation of staple leg 202a. Central bridge portion 118a is disposed between spine portions 118e of first and second staple-leg forming cavities 118b, 118c and extends upwardly or ascends from a bottom surface of first and second staple-leg forming cavities 118b, 118c of staple pocket 118 to facilitate forming of legs 200a of a staple 200 into a formed shape such as a B-shape seen in FIG. 9B. Each staple pocket 118 further includes an end wall 118f that extends linearly along a medial side of spine portions 118e of first and second staple-leg forming cavities 118b, 118c and central bridge portion 118a of staple pocket 118 (e.g., parallel to the longitudinal axis "L-L") to help guide formation of staple legs 200a to one side of backspan 204 of staple 200. End wall 118f may be parallel to the longitudinal axis "L-L" of anvil 110. Guide portion 118d and spine portion 118e of each biased staple-forming pocket 118 are separated by a centerline "CL" of the respective biased staple-forming pockets 118. The centerline "CL" may extend longitudinally through each of biased staple-forming pockets 118 within a respective row of biased staple-forming pockets 118 of anvil 110. Guide portion 118d is positioned away from knife slot 116 and spine portion 118e is positioned toward knife slot 116 and opposite to guide portion 118d.

Figure 9A:
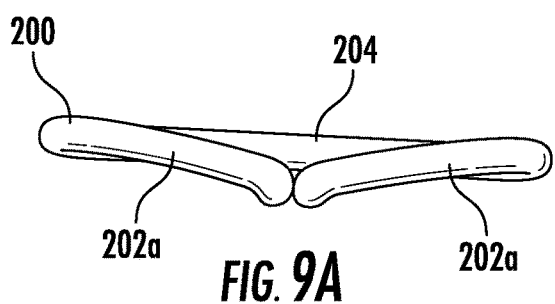
FIG. 9A is a top, perspective view of a staple formed by the staple pocket of FIG. 8.
Figure 9B:
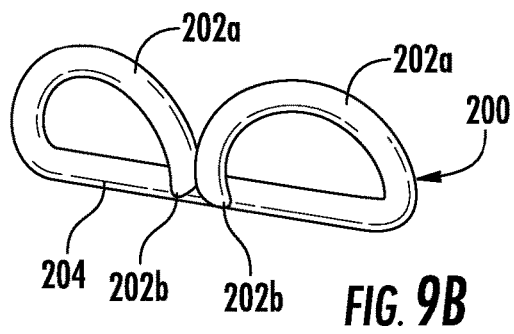
FIG. 9B is front, perspective view of the staple of FIG. 9A.

Referring also to FIGS. 9A and 9B, a firing of surgical stapling apparatus 10 causes rows of staples 200 to form against the rows of biased staple-forming pockets 118. In particular, each staple 200 aligns with one of biased staple-forming pockets 118 such that upon a firing of surgical stapling apparatus, staples legs 202a (e.g., two) of each staple 200 cam along the respective guide portions 118d of a corresponding biased staple-forming pocket 118 and funnel toward spine portion 118e of the corresponding biased staple-forming pocket 118 so that both staple legs 202a, including tips 202b of staple legs 202a, are formed to one side of backspan 204 of the respective staple 200. Specifically, the rows of biased staple-forming pockets 118 are arranged so that both legs 202a of all the staples are formed (e.g., in a B-shape) so that tips 202b of staples 200 are disposed on a medial side of the respective backspans 204 of staples 200 relative to anvil 110 (e.g., closer to knife slot 116 of anvil 110 or staple line knife cut) to hemostatically seal off blood flow and prevent staple tip punctures that create leak paths.

In some embodiments, anvil 110 is made at least partially from a rigid material such a stainless-steel material. In some embodiments, top surface 110c of anvil 110 may have a radial surface measuring from about R.150 inches to about R.165 inches. In some embodiments, anvil 110 may have a cross-sectional height of from about 0.070 inches to about 0.080 inches as measured vertically between top and bottom surfaces 110c, 110d, for instance at point midway along a longitudinal length of anvil 110.

In various embodiments, first and second staple-leg forming cavities 118b, 118c of anvil 110 may have a depth from about 0.002 inches to about 0.020 inches.

In embodiments, the pitch, for example, between central bridge portions 118a of adjacent biased staple-forming pockets 118 or from one biased staple-forming pocket 118 to the next in a given longitudinally-extending row may be from about 0.150 inches to about 0.160 inches. In some embodiments, biased staple-forming pockets 118 in a row are longitudinally offset from an adjacent row of biased staple-forming pockets 118 at least ½ of the pitch between adjacent biased staple-forming pockets 118 in a given row.

In embodiments, a width of anvil 110 defined across the rows of biased staple-forming pockets 118 may be about 0.255 inches, and in certain embodiments, not more than 0.255 inches. In some embodiments, distance between centerlines of adjacent rows of biased staple-forming pockets 118 may be about 0.042 inches, and in certain embodiments, not more than 0.042 inches. In embodiments, the distance between a centerline of an inner row of biased staple-forming pockets 118 and a centerline of knife slot 116, which is coincident with the longitudinal axis "L-L," may be about 0.042 inches, and in some embodiments, not more than 0.042 inches. In some embodiments, not less than 1½ of biased staple-forming pockets 118 are disposed proximal to a distal end of tissue stops 112, 114 on either side of knife slot 116.

Further, although illustrated and described in connection with an endoscopic linear surgical stapling apparatus, the disclosed staple pocket arrangement may be utilized on any suitable surgical stapling apparatus such as an open surgical stapling apparatus, a transverse surgical stapling apparatus, and/or a circular stapling apparatus.

Securement of any of the components of the presently disclosed apparatus may be effectuated using known securement techniques such welding, crimping, gluing, fastening, etc.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. An end effector for a surgical stapling apparatus, the end effector comprising:
   a cartridge assembly supporting a plurality of staples, each staple of the plurality of staples including a backspan, a first leg, and a second leg, the first and second legs extending from the backspan; and
   an anvil assembly coupled to the cartridge assembly, the anvil assembly including an anvil having opposed side surfaces and defining a longitudinal axis along a length of the anvil, the anvil defining a knife slot and a plurality of biased staple-forming pockets disposed between the opposed side surfaces of the anvil, each biased staple-forming pocket of the plurality of biased staple-forming pockets positioned to form the first and second legs of a respective staple of the plurality of staples on one side of the backspan of the respective staple, the one side of the backspan being positioned toward the knife slot of the anvil relative to the opposed side surfaces of the anvil, each biased-staple forming pocket including a first staple-leg forming cavity, a second staple-leg forming cavity, and an end wall that extends linearly along the first and second staple forming cavities, the end wall being parallel to the longitudinal axis of the anvil.

2. The end effector of claim 1, wherein the plurality of biased staple-forming pockets is arranged in at least one linear row.

3. The end effector of claim 2, wherein the at least one linear row includes an inner row and an outer row.

4. The end effector of claim 3, wherein the inner and outer rows are longitudinally offset from one another.

5. The end effector of claim 1, further comprising a dissecting tip that extends distally from the anvil.

6. The end effector of claim 1, wherein each of the first and second staple-leg forming cavities includes a guide portion and a spine portion, the guide portion configured to funnel one of the first or second legs of one of the staples of the plurality of staples toward the spine portion.

7. The end effector of claim 6, wherein the first and second staple-leg forming cavities are separated by a central bridge portion.

8. The end effector of claim 7, wherein the central bridge portion ascends from a bottom surface of the first and second staple-leg forming cavities.

9. The end effector of claim 8, wherein the end wall extends linearly along the central bridge portion on a medial side toward the knife slot.

10. A surgical stapling apparatus, comprising:
    a housing assembly; and
    a shaft assembly operatively coupled to the housing assembly and supporting an end effector, the end effector including:
       a staple cartridge supporting a plurality of staples, each staple of the plurality of staples including a backspan, a first leg, and a second leg, the first and second legs extending from the backspan; and
       an anvil having opposed side surfaces and defining a longitudinal axis along a length of the anvil, the anvil defining a knife slot and a plurality of biased staple-forming pockets positioned adjacent to the knife slot, the knife slot and the plurality of biased staple-forming pockets disposed between the opposed side surfaces of the anvil, each biased-staple forming pocket including a first staple-leg forming cavity, a second staple-leg forming cavity, and an end wall that extends linearly along the first and second staple forming cavities, the end wall being parallel to the longitudinal axis of the anvil, each biased staple-forming pocket of the plurality of biased staple-forming pockets configured to form the first and second legs of a respective staple of the plurality of staples on one side of the backspan of the respective staple, the one side of the backspan being positioned toward the knife slot of the anvil relative to the opposed side surfaces of the anvil.

11. The surgical stapling apparatus of claim 10, wherein the plurality of biased staple-forming pockets is arranged in linear rows on opposite sides of the knife slot.

12. The surgical stapling apparatus of claim 11, wherein the linear rows include an inner row and an outer row on each of the opposite sides of the knife slot.

13. The surgical stapling apparatus of claim 10, further comprising a dissecting tip that extends distally from the anvil.

14. The surgical stapling apparatus of claim 10, wherein the first and second staple-leg forming cavities are separated by a central bridge portion.

15. The surgical stapling apparatus of claim 14, wherein the end wall is disposed in parallel relation to the knife slot.

* * * * *